(12) United States Patent
Blanco et al.

(10) Patent No.: US 10,569,067 B2
(45) Date of Patent: Feb. 25, 2020

(54) CONTROLLED RELEASE NANOPARTICULATE MATTER DELIVERY SYSTEM

(71) Applicants: Raytheon Company, Waltham, MA (US); Board of Regents, The University of Texas System, Austin, TX (US)

(72) Inventors: Letia M. Blanco, Carrollton, TX (US); Kyle C. Godfrey, Garland, TX (US); Christopher A. Grace, Coppell, TX (US); Christopher B. Alberts, Glenn Heights, TX (US); Andrew E. Patin, Lewisville, TX (US); Panayiotis S. Shiakolas, Irving, TX (US); Pranesh B. Aswath, Grapevine, TX (US)

(73) Assignees: RAYTHEON COMPANY, Waltham, MA (US); THE BOARD OF REGENTS, THE UNIVERSITY OF TEXAS SYSTEM, Austin, TX (US)

( * ) Notice: Subject to any disclaimer, the term of this patent is extended or adjusted under 35 U.S.C. 154(b) by 85 days.

(21) Appl. No.: 15/348,358

(22) Filed: Nov. 10, 2016

(65) Prior Publication Data
US 2017/0056634 A1 Mar. 2, 2017

Related U.S. Application Data

(62) Division of application No. 13/849,060, filed on Mar. 22, 2013, now Pat. No. 9,522,241.
(Continued)

(51) Int. Cl.
*A61M 35/00* (2006.01)
*A61M 1/00* (2006.01)
(Continued)

(52) U.S. Cl.
CPC ........... *A61M 35/00* (2013.01); *A61K 9/0004* (2013.01); *A61K 9/7092* (2013.01);
(Continued)

(58) Field of Classification Search
CPC ............... A61K 9/0004; A61K 9/7092; A61M 2205/3368; A61M 2205/36;
(Continued)

(56) References Cited

U.S. PATENT DOCUMENTS 7,699,834 B2 * 4/2010 Hood .................. A61K 9/0004
604/892.1
2002/0174660 A1 11/2002 Venkatasubramanian
(Continued)

FOREIGN PATENT DOCUMENTS

WO 2009126442 A1 10/2009

*Primary Examiner* — Quynh-Nhu H. Vu
(74) *Attorney, Agent, or Firm* — Cantor Colburn LLP

(57) ABSTRACT

A controlled release nanoparticulate matter delivery system includes a plurality of thermoresponsive modules containing a respective nanoparticulate matter. Each thermoresponsive module is selectively operable in at least one of a heating mode that releases the nanoparticulate matter and a cooling mode that inhibits release of the nanoparticulate matter. A control module is in electrical communication with the plurality of thermoresponsive modules. The control module is configured to determine a temperature of each thermoresponsive module and to select the at least one heating mode and cooling mode based on the temperature. The heating and cooling mode may be selected in response to a desired dosing profile and/or a biometric condition.

6 Claims, 10 Drawing Sheets

Related U.S. Application Data

Figure 1:
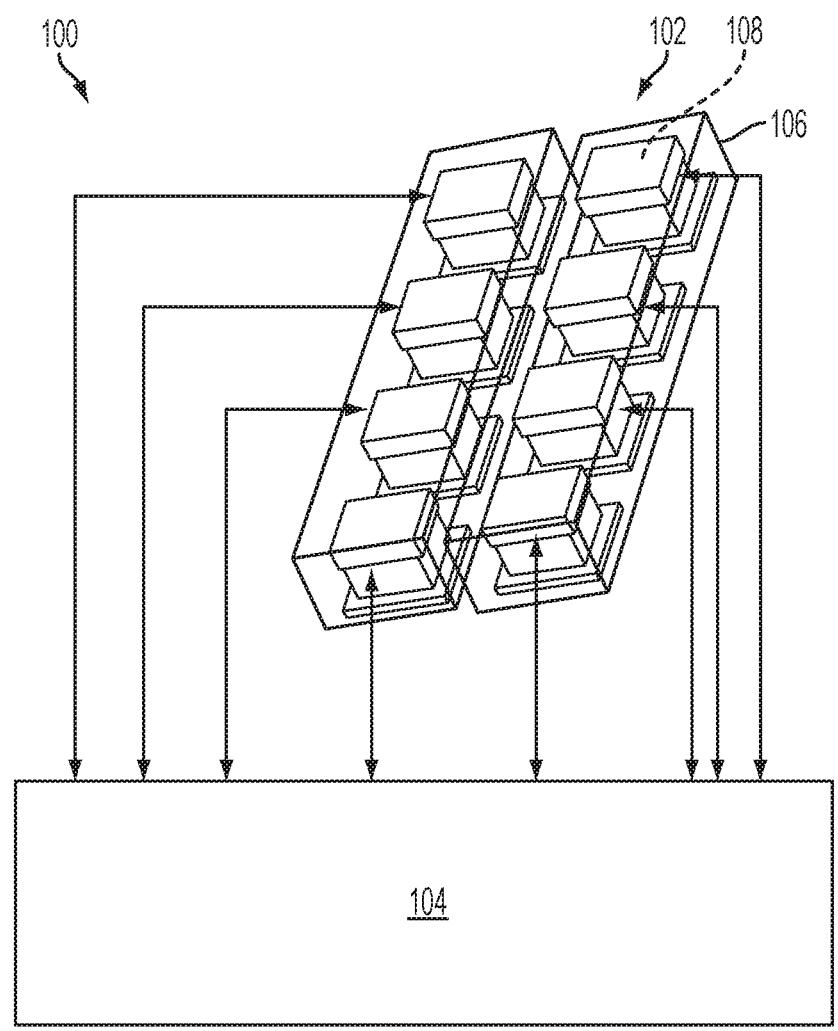

(60) Provisional application No. 61/614,120, filed on Mar. 22, 2012.

(51) Int. Cl.
| | | |
|---|---|---|
| *A61K 9/00* | (2006.01) | |
| *A61K 9/70* | (2006.01) | |
| *A61M 5/44* | (2006.01) | |

(52) U.S. Cl.
CPC ............ *A61M 1/0023* (2013.01); *A61M 5/44* (2013.01); *A61M 2205/3368* (2013.01); *A61M 2205/36* (2013.01); *A61M 2205/3673* (2013.01); *A61M 2205/50* (2013.01); *A61M 2205/502* (2013.01); *A61M 2205/52* (2013.01); *A61M 2230/005* (2013.01); *A61M 2230/06* (2013.01); *A61M 2230/42* (2013.01); *A61M 2230/50* (2013.01)

(58) Field of Classification Search
CPC ...... A61M 2205/3673; A61M 2205/50; A61M 2205/502; A61M 2205/52; A61M 2230/005; A61M 35/00; A61M 5/44
See application file for complete search history.

(56) References Cited

U.S. PATENT DOCUMENTS

| | | | |
|---|---|---|---|
| 2005/0076944 A1* | 4/2005 | Kanatzidis | H01L 35/16 136/239 |
| 2008/0050435 A1* | 2/2008 | Hennink | A61K 9/1075 424/486 |
| 2008/0138408 A1* | 6/2008 | Venkatesh | A61K 31/70 424/464 |
| 2009/0014433 A1 | 1/2009 | O'Neil et al. | |
| 2010/0172990 A1* | 7/2010 | Forcada Garcia | A61K 9/5138 424/486 |
| 2010/0256824 A1* | 10/2010 | Val-Khvalabov | F24F 3/14 700/282 |
| 2012/0310151 A1* | 12/2012 | Takahata | A61M 5/44 604/58 |

* cited by examiner

CONTROLLED RELEASE NANOPARTICULATE MATTER DELIVERY SYSTEM

CROSS REFERENCE TO RELATED APPLICATIONS

This application is a divisional application of U.S. patent application Ser. No. 13/849,060, filed on Mar. 22, 2013, which is a non-provisional of and claims priority to U.S. Application Ser. No. 61/614,120, entitled "CONTROLLED RELEASE NANOPARTICULATE MATTER DELIVERY", filed Mar. 22, 2012, the disclosures of which are incorporated by reference herein in their entireties.

BACKGROUND

The present disclosure relates generally to a liquid agent delivery system and, more particularly, to an electronically controlled release system to a deliver a liquid agent.

Conventional liquid agent delivery devices, such as a transdermal medical device, typically consist of a medicated adhesive patch that is placed on a patient's skin or wound to deliver medication. The medication is then absorbed through the skin and into the bloodstream to treat the patient. Conventional transdermal medical devices, however, are incapable of controlling the dosage applied to the skin or wound. For example, the medication may be released from the patch at an uncontrollable rate. Furthermore, the dosage of the medication is released regardless of the biometrics of the patient.

SUMMARY

In an exemplary embodiment, a controlled release nanoparticulate matter delivery system comprises a plurality of thermoresponsive modules containing a respective nanoparticulate matter. Each thermoresponsive module is selectively operable in at least one of a heating mode that releases the nanoparticulate matter and a cooling mode that inhibits release of the nanoparticulate matter. The delivery system further comprises a control module in electrical communication with the plurality of thermoresponsive modules. The control module is configured to determine a temperature of each thermoresponsive module and to select the at least one heating mode and the cooling mode based on the temperature.

In another embodiment, a thermoresponsive module to release a nanoparticulate matter comprises a thermoelectric device and a hydrocomposite carrier. The thermoelectric device includes a variable temperature surface, and is selectively operable in at least one of a heating mode to heat the surface and a cooling mode to cool the surface. The hydrocomposite carrier is configured to deliver the nanoparticulate matter based on the temperature of the variable temperature surface.

In still another embodiment, a method of releasing nanoparticulate matter contained in a thermoresponsive polymer comprises determining a desired release rate at which to release the nanoparticulate matter, and determining a desired temperature at which the nanoparticulate matter is released at the desired release rate. The method further comprises determining an actual temperature of the thermoresponsive polymer, and comparing the actual temperature to the desired temperature. The method further includes adjusting the actual temperature of the thermoresponsive polymer to control the release of the nanoparticulate matter based on the comparison between the actual temperature and the desired temperature.

BRIEF DESCRIPTION OF THE DRAWINGS

For a more complete understanding of this disclosure, reference is now made to the following brief description, taken in connection with the accompanying drawings and detailed description, wherein like reference numerals represent like parts:

FIG. 1 is a block diagram of a controlled release nanoparticulate matter delivery system according to an exemplary embodiment of the disclosure;

FIG. 2 illustrates a diagram of hydrocomposite carrier including a thermoresponsive polymer containing nanoparticulate matter according to an exemplary embodiment of the disclosure;

FIG. 3A is a block diagram illustrating a thermoresponsive module according to an exemplary embodiment of the disclosure;

FIG. 3B is an exploded view of a thermoresponsive module illustrated in FIG. 3A;

FIG. 4A is a diagram of a thermoelectric device operating in a first mode according to an exemplary embodiment of the disclosure;

FIG. 4B is a diagram of a thermoelectric device operating in a second mode according to an exemplary embodiment of the disclosure;

FIG. 5 illustrates a controlled release nanoparticulate matter delivery system according to another exemplary embodiment of the disclosure;

FIG. 6 is a flow diagram illustrating a method of releasing nanoparticulate matter according to an exemplary embodiment of the disclosure;

FIG. 7 is a flow diagram illustrating another method of releasing nanoparticulate matter according to an exemplary embodiment of the disclosure; and FIG. 8 is a flow diagram illustrating still another method of releasing nanoparticulate matter according to an exemplary embodiment of the disclosure.

DETAILED DESCRIPTION

It will be appreciated that for simplicity and clarity of illustration, where appropriate, reference numerals have been repeated among the different figures to indicate corresponding or analogous elements. In addition, numerous specific details are set forth in order to provide a thorough understanding of the embodiments described herein. However, it will be understood by those of ordinary skill in the art that the embodiments described herein can be practiced without these specific details. In other instances, methods, procedures and components have not been described in detail so as not to obscure the related relevant feature(s) being described. Also, the description is not to be considered as limiting the scope of the embodiments described herein.

Referring now to FIG. 1, a block diagram of a controlled release nanoparticulate matter delivery system 100 according to an exemplary embodiment of the disclosure. The delivery system 100 includes a plurality of thermoresponsive modules 102 and a control module 104. The thermoresponsive modules 102 contain a respective nanoparticulate matter. The thermoresponsive modules 102 may contain the same type of nanoparticulate matter, or may contain a different type of nanoparticulate matter. In addition, the delivery system may include a combination of thermoresponsive modules 102, each containing different types of nanoparticulate matter. The nanoparticulate matter may include a therapeutic nanoparticulate matter including, but not limited to, antimicrobial agents, analgesics, and growth hormones. It is to be appreciated that the nanoparticulate matter is not limited to any particular mass and/or density of the nanoparticulate matter. In at least one embodiment, the nanoparticulate matter is an aqueous therapeutic nanoparticulate matter, such as a liquid-based medication. The liquid-based medication may be introduced to the skin or wound of a subject, such as a human patient for example, where it is absorbed into the bloodstream.

Referring further to FIG. 1, each thermoresponsive module 102 is configured to selectively operate in a heating mode and a cooling mode. The heating mode releases the nanoparticulate matter from the thermoresponsive module 102 so it may be delivered to the skin or a wound. The cooling mode, however, inhibits release of the nanoparticulate matter such that it is withheld in thermoresponsive module 102.

More specifically, the thermoresponsive module 102 includes a housing 106, and a hydrocomposite carrier 108 that contains the nanoparticulate matter. The hydrocomposite carrier 108 is disposed in the housing 106 such that a surface of the hydrocomposite carrier 108 is capable of contacting skin or wound. When operating in the heating mode, the nanoparticulate matter is released from the hydrocomposite carrier 108 and permeates there through to contact the skin or wound. When operating in the cooling mode, however, the nanoparticulate matter is inhibited from permeating through the hydrocomposite carrier 108, as discussed in greater detail below.

Figure 2:
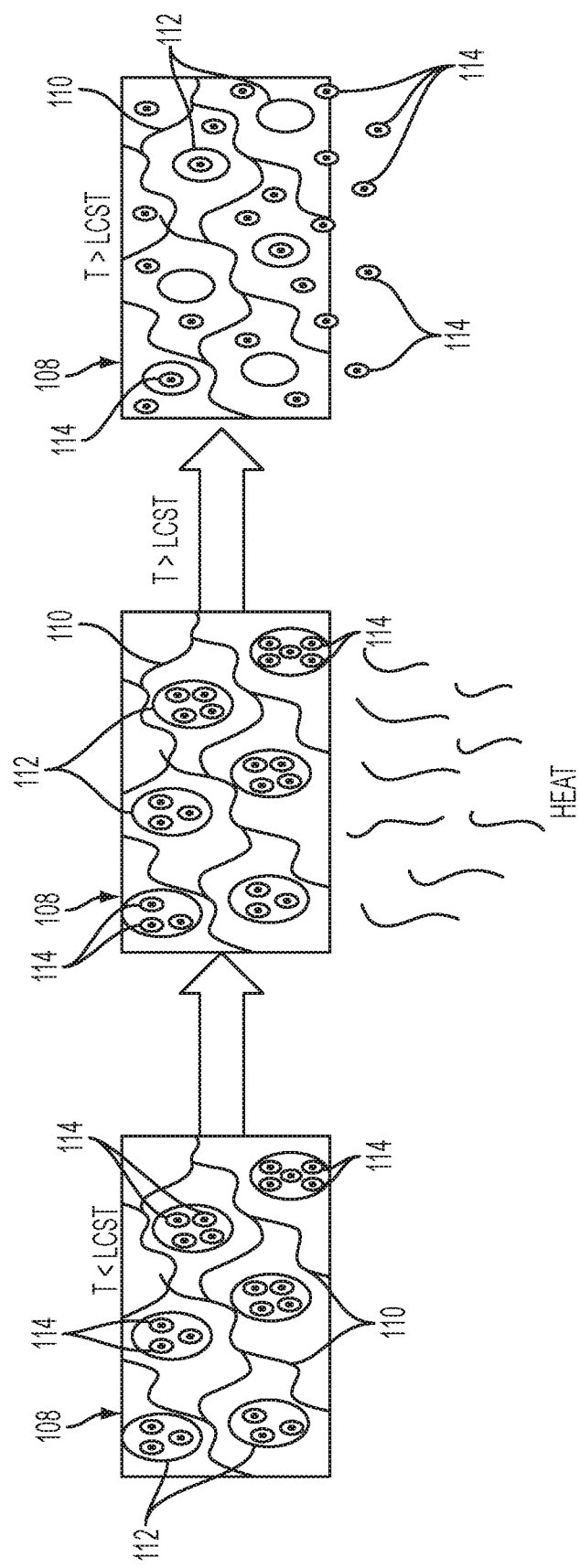

Referring to FIG. 2, the hydrocomposite carrier 108 may include a thermally responsive composite hydrogel material 110. In at least one example, the composite hydrogel material 108 comprises one or more thermoresponsive polymers 112 containing an aqueous nanoparticulate matter 114, a photo-initiator, such as for example Irgacure 2959, and a matrix polymer. In at least one embodiment of the disclosure, the thermoresponsive polymer 112 is formed from Poly[N-isopropylacrylamide-co-acrylamide] (PNIPAM-AA).

The thermoresponsive polymers 112 i.e., the PNIPAM-AAm 112, experience a phase change based on the temperature of the polymer 112. More specifically, when the thermoresponsive polymer 112 is below a first temperature, i.e., a lower critical solution temperature (LCST), the PNIPAM-AAm 112 is hydrophilic. Accordingly, the PNIPAM-AAm 112 inhibits the release of the aqueous nanoparticulate matter 114 and allows the thermoresponsive polymer 112 to remain loaded. The hydrogel 110 may be exposed to heat, which thereby heats the thermoresponsive polymer 112. When the temperature of the thermoresponsive polymer 112 exceeds the LCST, the PNIPAM-AAm 112 becomes hydrophobic and rejects the aqueous nanoparticulate matter 114 into the surrounding hydrogel 110. Accordingly, the nanoparticulate matter 114 permeates through the hydrogel 110 where it contacts the skin. Thermal insulation agents may be added to the hydrogel 110 to vary the LCST. For example, acrylamide may be added to the hydrogel 110 to increase the LCST of the PNIPAM-AAm 112 from about 80° F. to about 100° F., thus reducing the possibility that normal contact with skin or wound would not create enough heat to activate the hydrophobic state of the PNIPAM-AAm 112.

When the thermoresponsive polymer 112 is heated continuously at a temperature above the LCST, the nanoparticulate matter 114 experiences three types of release phases. An initial burst phase, a sustained burst phase, and a plateau release phase. The initial burst is completed in approximately the first hour from which the hydrophobic state of the thermoresponsive polymer 112 is activated. The initial burst phase releases the nanoparticulate matter 114 at the highest rate with respect to the three release phases. The sustained burst phase lasts approximately 1-8 hours and releases the nanoparticulate matter 114 at rate less than the initial burst phase. The plateau release phase releases the nanoparticulate matter 114 at rate less than each of the initial burst phase and the sustained burst phase, and may commence when the supply of nanoparticulate matter 114 stored in the thermoresponsive module 102 nears complete depletion. By selectively exposing the hydrogel 110 to cycles of heating and cooling, the amount of nanoparticulate matter 114 released during each of the three phases, and in particular the initial burst phase, may be controlled to provide a "uniform dosing" of the nanoparticulate.

The control module 104 is in electrical communication with each of the thermoresponsive modules 102. In general, the term "module", as used herein, refers to logic embodied in hardware or firmware, or to a collection of software instructions, written in a programming language including, but not limited to, Java, C, or assembly, and which is executed by a microprocessor. One or more software instructions in the modules may be embedded in firmware, such as, for example, in an EPROM, and/or stored in any type of non-transitory computer-readable medium or other storage device. In addition, the control module 104 may include a battery powered mobile field programmable gate array, which allows the delivery system 100 to be easily coupled to the subject, without restricting the subject's mobility. The control module 104 may further be programmed with a desired dosing profile. That is, the memory of the control module 104 may be stored with one or more desired profiles indicative of the release rate, release time, release amount, etc., of the nanoparticulate matter 114 stored in one or more thermoresponsive modules 102. Accordingly, the release of the nanoparticulate matter 114 may be controlled according to the respective dosing profile.

In at least one embodiment, the control module may control one thermoresponsive module 102 individually with respect to a different thermoresponsive module 102. The control module 104 may also control groups of thermoresponsive modules 102 individually from different groups, or may control all of the thermoresponsive modules 102 at one time. The control module 104 may be configured to determine a temperature of each thermoresponsive module 102 and/or one or more biometric conditions, and to select at least one heating mode or cooling mode based on the temperature and/or biometric conditions. In addition, the control module 104 may control the dosing amounts, release rates and/or release times of the nanoparticulate matter 114, as discussed in greater detail below.

Figure 3A:
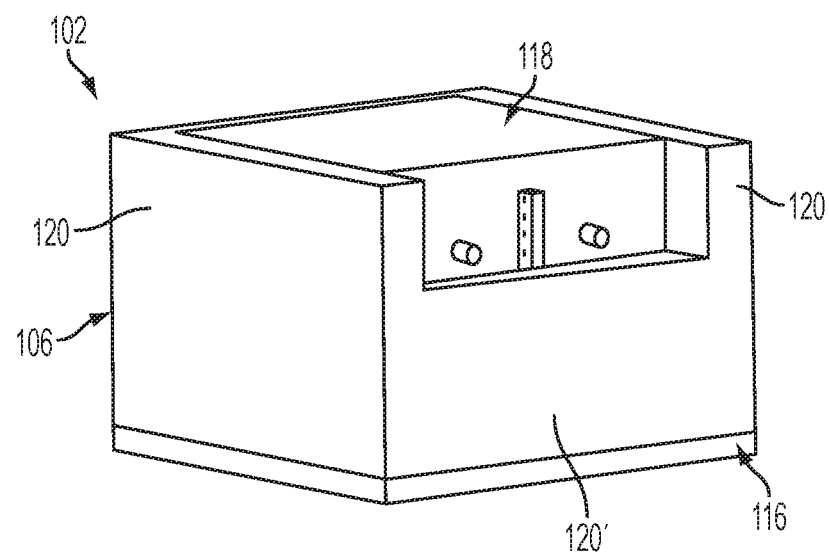
Figure 3B:
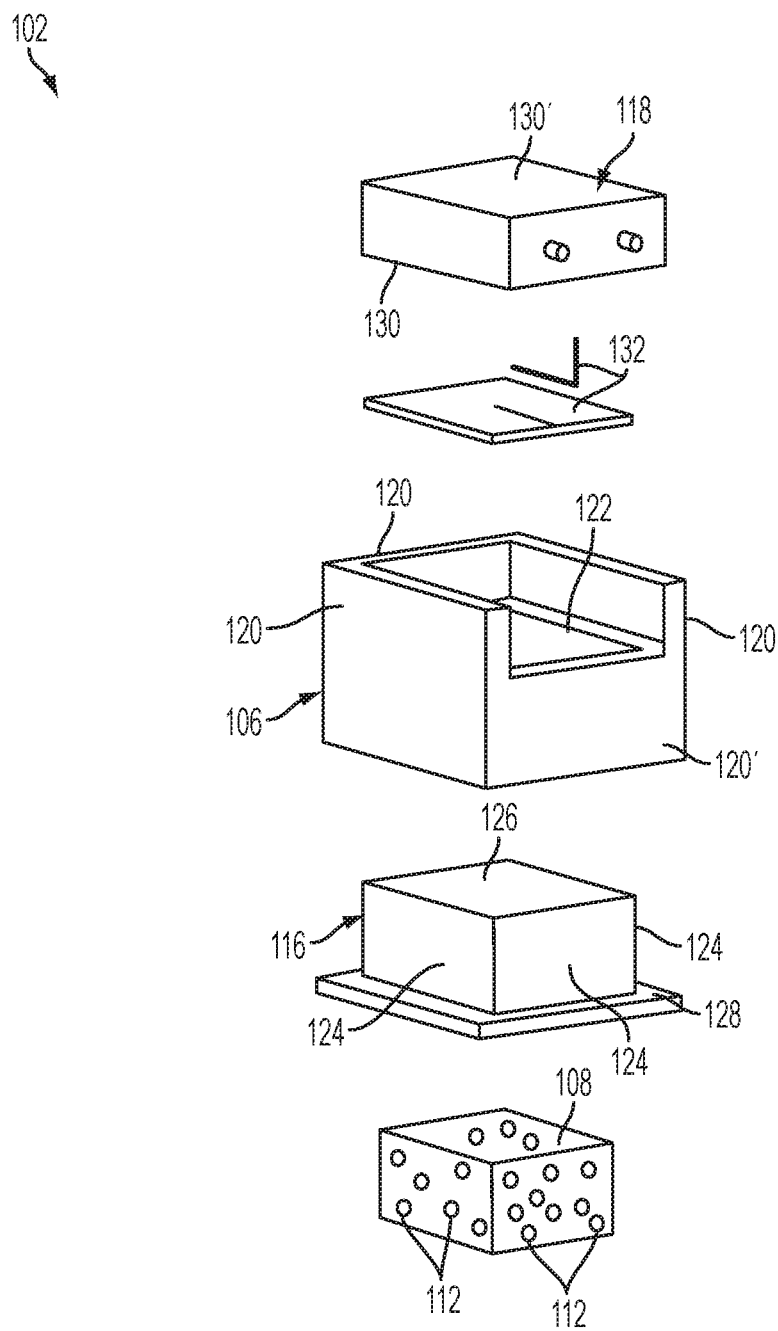

Referring now to FIGS. 3A-3B, a thermoresponsive module 102 is illustrated according to an exemplary embodiment of the disclosure. The thermoresponsive module 102 includes a housing 106, a tray 116, a thermoelectric device 118, and a hydrocomposite carrier 108. The housing 106 includes a plurality of walls 120 defining an opening that extends between a first end of the housing and a second end opposite the first end. At least one wall 120' has a length shorter than the remaining walls to define a clearance between the at least one wall 120' and the first end. The housing further includes a ledge 122 extending from an inner surface of the housing into the opening. The ledge 122 defines a first opening and a second opening. The first opening extends between the second end and the ledge 122. The second opening is larger than the first opening, and extends between the ledge 122 and the first opening. In at least one exemplary embodiment, the housing is formed of poly(methyl methacrylate) (PMMA).

The tray 116 includes a plurality of sides 124 defining an open bottom and a solid top surface 126 opposite the open bottom to define an inner cavity. A base 128 surrounds the open bottom. The tray 116 is disposed at the second opening of the housing 106 such that the base 128 supports the housing 106, and the sides 124 of the tray 116 extend into the first opening. The tray 116 is formed from a thermally conductive material including, but not limited to, aluminum and steel. Accordingly, the tray 116 may transfer heat received at one or more of the sides 124 into the internal cavity. In at least one embodiment, the tray 116 may be removed from the thermoresponsive module 102. Accordingly, the thermoresponsive module 102 may be cleaned and sterilized, and the tray 116 may be reloaded with nanoparticulate matter before being replaced.

Figure 4A:
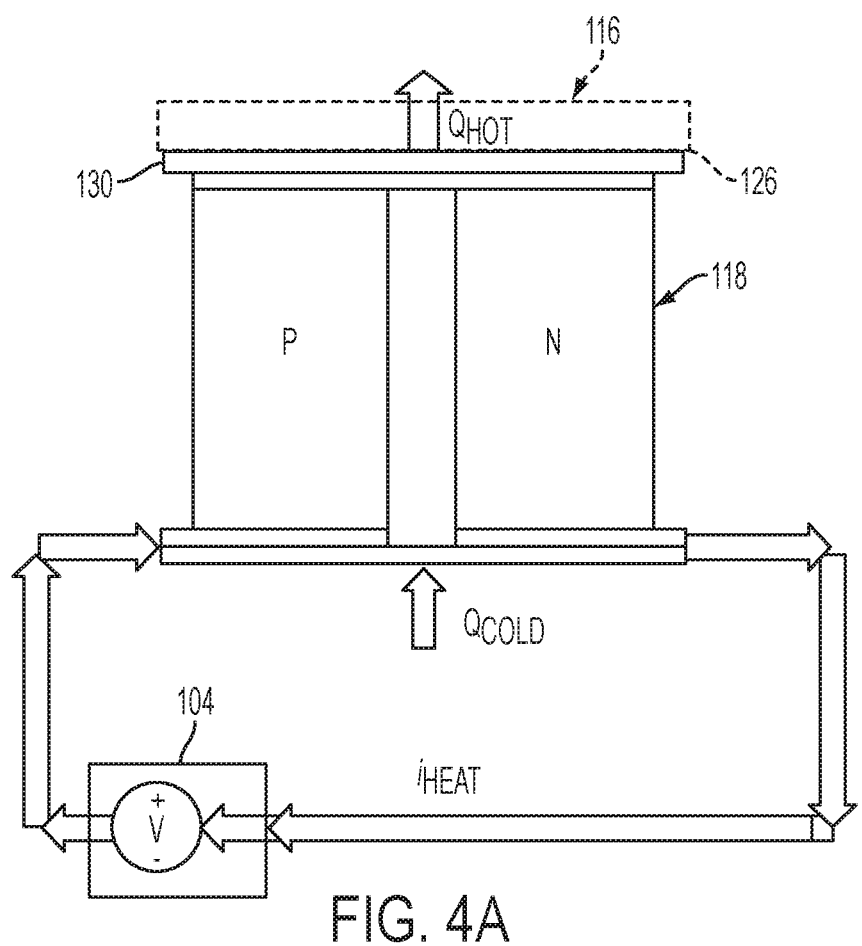
Figure 4B:
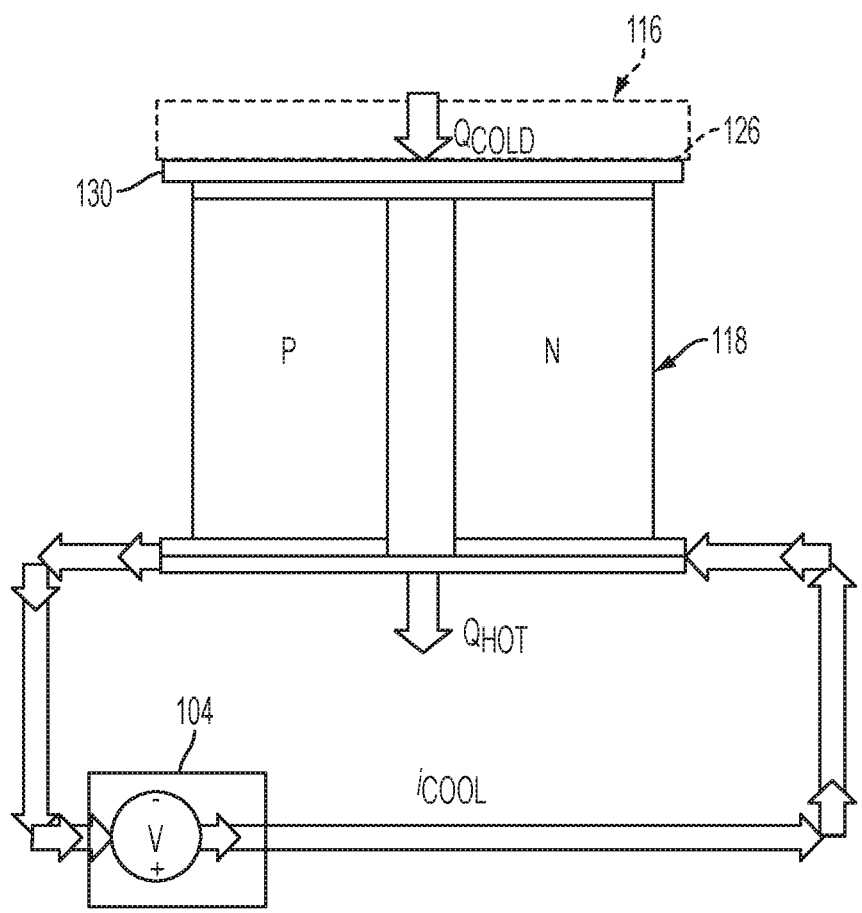

The thermoelectric device 118 includes at least one thermal surface 130, 130' that varies in temperature based on an operating mode of the thermoelectric device 118. More specifically, the thermoelectric device 118 is configured to operate in at least one of a heating mode and a cooling mode based on the flow of the current. When current flows in a first direction (e.g., $i_{HEAT}$) through the thermoelectric device 118, the thermal surface 130 is heated such that the thermoelectric device 118 emits heat therefrom as illustrated in FIG. 4A. However, when current flows in a second direction opposite the first direction (e.g., $i_{COOL}$), the thermal surface 130 is cooled as illustrated in FIG. 4B. In at least one embodiment, the control module 104 is electrically connected to the thermoelectric device 118. The control module 104 generates a first voltage having a first polarity, which thereby induces the current to flow in the first direction. To generate the current flow in the second direction, the control module 104 generates a voltage having an opposite polarity. In at least one embodiment, the thermoelectric device 118 is a thermoelectric Peltier device, which is well-known by those of ordinary skill in the art and operates according to a Peltier effect generally described above.

The thermoelectric device 118 is disposed at the first opening and is supported by the ledge 122 such that the thermal surface 130 is in thermal communication with the top surface 126 of the tray 116 through a thermal sensor. Accordingly, when the thermoelectric device 118 operates in the heating mode, heat from the top surface 126 of the tray 116 is transferred into the inner cavity. When the thermoelectric device 118 operates in the cooling mode, however, the top surface 126 of the tray 116 is cooled, thereby cooling the inner cavity.

The hydrocomposite carrier 108 is disposed in the cavity of the tray 116 to deliver the nanoparticulate matter 114 therefrom. As discussed in detail above, the composite hydrogel material 110 comprises one or more thermoresponsive polymers 112 containing the aqueous nanoparticulate matter 114. The nanoparticulate matter 114 is released based on the temperature of the thermoresponsive polymers 112. By disposing the hydrocomposite carrier 108 in the inner cavity of the tray 116, the temperature of the thermoresponsive polymers 112 may be selectively varied via the thermoelectric device 118 to selectively release the nanoparticulate matter 114.

In at least one embodiment, the thermoresponsive module 102 may further include a thermal sensor 132 interposed between the thermoelectric device 118 and the top surface 126 of the tray 116. The thermal sensor 132 may include, but is not limited to, a thermocouple. The thermal sensor 132 may be in electrical communication with the control module 104 to output a voltage signal in response to the heat to indicate a temperature at the thermoelectric device 118. The control module 104 may include memory that stores a release temperature value, i.e., the LCST, to determine the temperature at which the thermoresponsive polymer 112 releases the nanoparticulate matter 114. During operation, the thermal sensor 132 may output a voltage indicative of the actual temperature of the thermoresponsive polymer 112. The control module 104 may compare the actual temperature to the stored release temperature, and may control the flow of current ($i_{COOL}$ or $i_{HEAT}$) to the thermoelectric device 118. Accordingly, the temperature of the thermoresponsive polymer 112 may be varied, and the release of the nanoparticulate matter 114 from one or more of the thermoresponsive modules 102 may be controlled.

Figure 5:
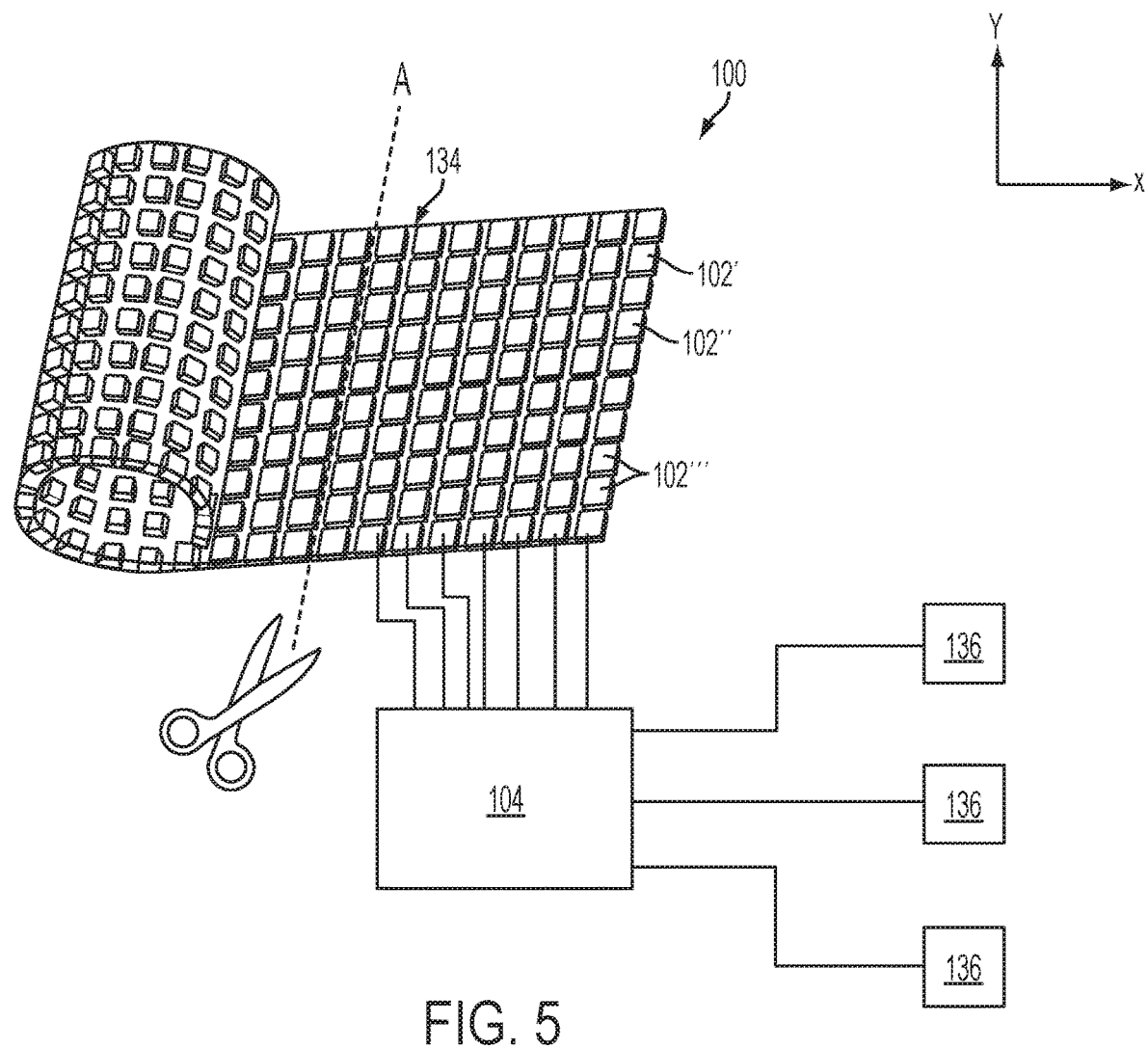

Referring now to FIG. 5, a controlled release nanoparticulate matter delivery system 100 is illustrated according to another exemplary embodiment of the disclosure. The controlled release nanoparticulate matter 114 delivery system 100 illustrated in FIG. 5 includes a flexible bandage 134 that includes a plurality of thermoresponsive modules 102, which can release multiple medications on any time schedule, i.e., at any delivery time. As mentioned above, the release of the nanoparticulate matter 114 may be based on a desired dosing profile programmed in the control module 104 and/or stored in a memory. The memory may be integrated in the control module 104 and/or may be connected in electrical communication with the control module 104 via a removable memory storage device. In at least one example, a first thermoresponsive module 102' may be loaded with a first nanoparticulate matter, such as an antimicrobial, and may be released every hour. A second thermoresponsive module 102" may be loaded with a second different nanoparticulate matter, such as a growth hormone, and may be released every four hours. A third thermoresponsive module 102''' may be loaded with a third nanoparticulate matter, such as a pain killer, and may be released continuously without interruption. In addition, the thermoresponsive module 102, or at least a portion of the thermoresponsive module 102, such as tray discussed in detail above, may be removed from the bandage. Accordingly, the bandage 134 and/or the thermoresponsive module 102 may be cleaned and sterilized. In addition, the thermoresponsive module 102 may be reloaded with nanoparticulate and then returned to the bandage 134 without compromising the integrity of one or more electrical wires, which are discussed in greater detail below.

The width of the bandage extends along the Y-axis and may be fixed by the number of thermoresponsive modules 102 in a strip. The length of the bandage extends along the X-direction and may be customizable to the size of a treatment site, i.e., an area of the skin to be treated. Each module may be wired laterally in the Y-direction to define one or more strips, i.e., rows, extending several modules long. Each of these strips is independently wired so the bandage may be cut along a cutting axis (A), which extends along the Y-axis and in between strips. Accordingly, the size of the bandage may be customized without compromising the integrity of the wiring.

The delivery system 100 may further include at least one sensor 136 in electrical communication with the control module 104. The sensors 136 may determine at least one biometric condition of the subject that is to receive the nanoparticulate matter. The biometric condition includes, but is not limited to, body temperature, body perspiration, body vibration, breathing, heart rate and sound. Accordingly, the control module 104 controls at least one thermoresponsive module 102 to release the nanoparticulate matter in response to the detection of at least one biometric condition. For example, a sensor 136 may be coupled to the skin or wound of the subject, and may output a temperature signal indicative of the subject's body temperature. Based on the temperature signal, the control module 104 may determine the subject has a fever, and may therefore control at least one thermoresponsive module 102 loaded with fever-reducing medication to release the medication. In another embodiment, a plurality of sensors 136 may each detect a different respective biometric condition. Accordingly, the control module 104 may control individual thermoresponsive modules 102 to release a particular medication that treats the respective detected biometric condition.

Embodiments of the delivery system 100 may further include one or more sub-systems including, but not limited to, a thermal management system, an exudate removal system, and a graphic user interface (GUI). The thermal management system may be coupled with the bandage and/or one or more thermoresponsive modules to remove heat from the system. The thermal management system may include, but is not limited to, one or more heat sinks and a liquid cooling system. The liquid cooling system may be in electrical communication with the control module 104, and may be controlled according to the one or more sensors that detect a temperature associated with the delivery system 100.

The exudate removal system may be provided to remove bodily fluids released from a wound that is to be treated using the delivery system 100. The exudate removal system may include a piezoelectric pump and one or more microchannels. The pump may be in electrical communication with the control module to remove access bodily fluids from the delivery system via the microchannels.

The GUI may be included with the delivery system 100 and may provide various information to a subject and/or a person treating the subject. In at least one embodiment, the GUI is in electrical communication with the control module, and may provide information including, but not limited to, the type of nanoparticulate matter loaded in a particular thermoresponsive module, the amount of nanoparticulate matter remaining in a particulate module, the temperature of the subject and/or the thermoresponsive modules, information from the biometric sensors, the dosing times and/or release rates set for each thermoresponsive module, which thermoresponsive modules are actively releasing nanoparticulate matter, etc. In addition, the GUI may receive direct inputs that control the operation of the delivery system including, but not limited to, dosing times, release rates, enable/disable of particulate thermoresponsive modules, etc. Accordingly, precise control of the thermoresponsive module may be conveniently achieved.

Figure 6:
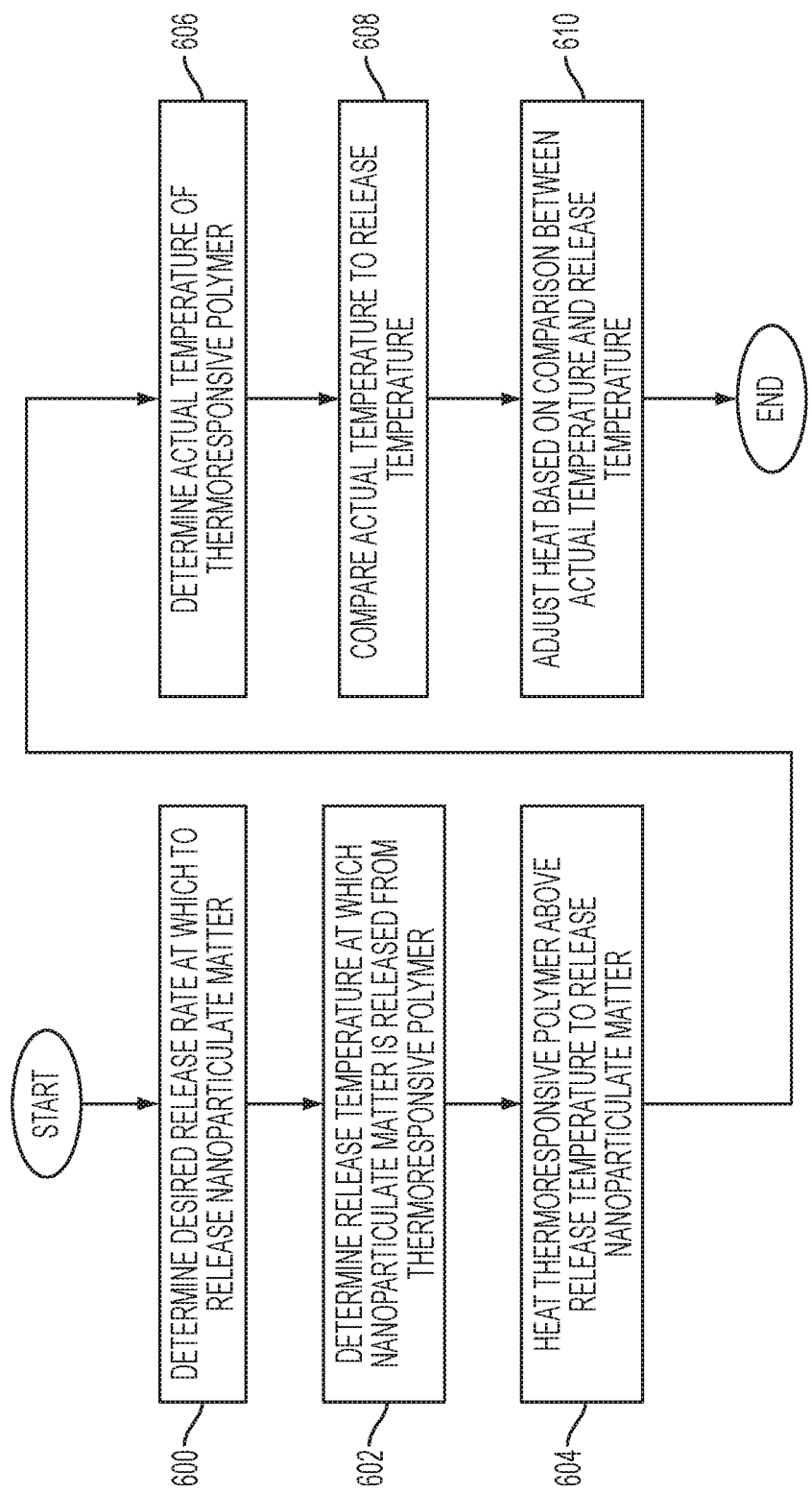

Referring now to FIG. 6, a flow diagram illustrates a method of releasing nanoparticulate matter according to an exemplary embodiment of the disclosure. At operation 600, a desired release rate at which to release nanoparticulate matter is determined. At operation 602, a release temperature is determined. The release temperature may include, for example, the LCST at which the thermoresponsive polymer becomes hydrophobic and releases the nanoparticulate matter contained therein. The thermoresponsive polymer is heated above the release temperature at operation 604. Accordingly, the nanoparticulate matter may be released from the nanoparticulate matter and may ultimately be delivered to a target area of the skin. At operation 606, the actual temperature of the thermoresponsive polymer is determined. The actual temperature is compared to the release temperature at operation 608. At operation 610, the heat provided to the thermoresponsive polymer may be adjusted and/or cut off based on the comparison in order to control the release rate of the nanoparticulate matter, and the operation ends. It is appreciated that the method described above is at least one example of releasing nanoparticulate matter, and other methods of controlling the release or inhibiting the release of the nanoparticulate matter based on the temperature of the thermoresponsive polymer may be realized. Further, it is appreciated that the method may be repeated for the duration of a dosage profile.

Figure 7:
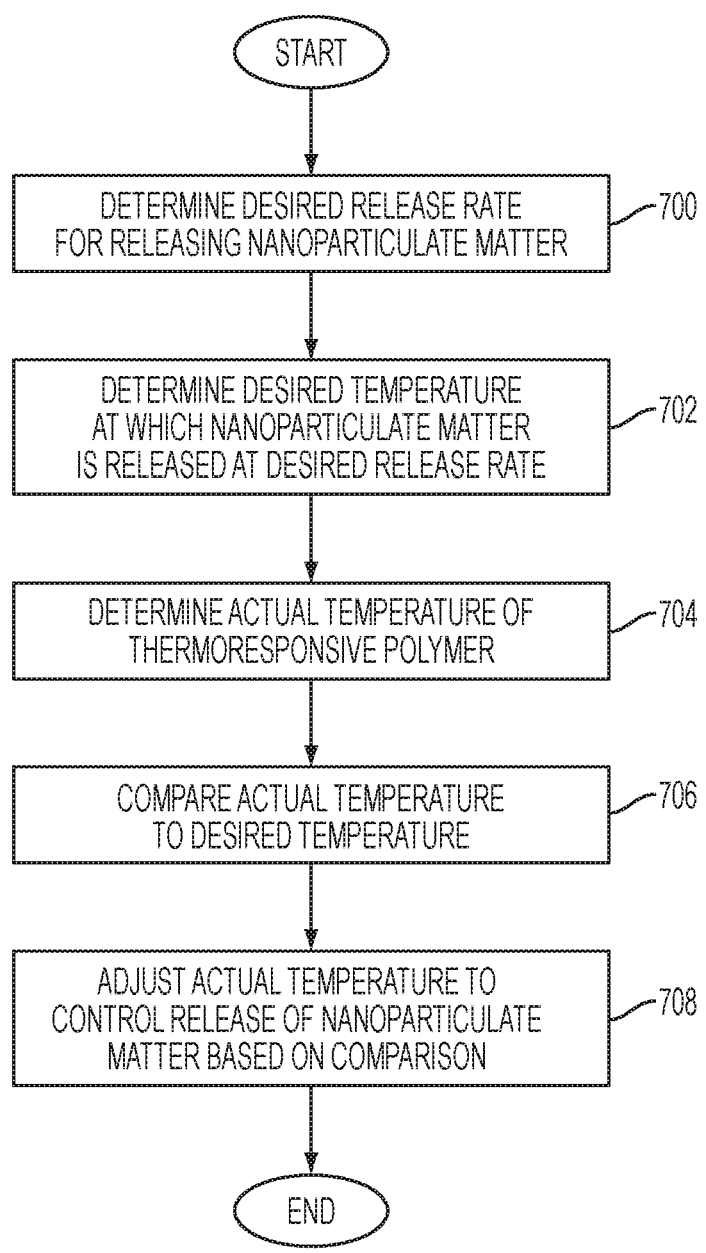

Referring now to FIG. 7, a flow diagram illustrates another method of releasing nanoparticulate matter contained in a thermoresponsive polymer. At operation 700, a desired release rate for releasing the nanoparticulate matter from the thermoresponsive polymer is determined. At operation 702, a desired temperature of the thermoresponsive polymer at which the nanoparticulate matter is released at the desired release rate is determined. A determination of the actual temperature, i.e., real-time temperature, of the thermoresponsive polymer is performed at operation 704. The actual temperature may then be compared to the desired temperature at operation 706. Based on the comparison, the actual temperature of the thermoresponsive polymer may be adjusted to control the release of nanoparticulate matter therefrom at operation 708, and the method ends. The actual temperature of the thermoresponsive polymer may control according to operation of the controlled release nanoparticulate matter delivery system described in detail herein. Moreover, it is appreciated that the method may be repeated for the duration of a dosage profile.

Figure 8:
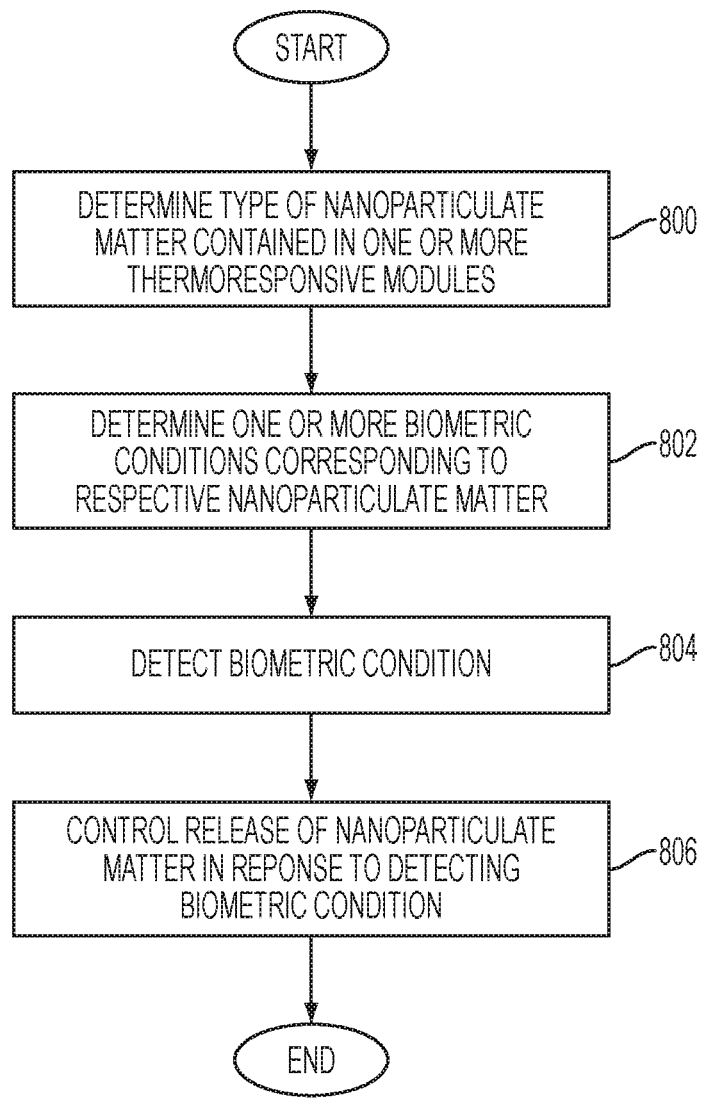

Turning now to FIG. 8, a flow diagram illustrates a method of releasing nanoparticulate matter contained in a thermoresponsive module according to at least one exemplary embodiment. More specifically, a type of nanoparticulate contained in one or more thermoresponsive modules is determined at operation 800. For example, one or more first thermoresponsive modules may contain fever reducing nanoparticulates, while one or more second thermoresponsive modules may contain antimicrobial nanoparticulates. At operation 802, one or more biometric conditions corresponding to a respective nanoparticulate matter are determined. For example, the fever reducing nanoparticulate may correspond to a biometric condition, such as a fever detected by excessive body temperature, while the antimicrobial nanoparticulate matter may correspond to formation of an infection detected by one or more sensors. At operation 804, one or more biometric conditions are detected. As mentioned above, the biometric condition may be detected by one or more sensors located near and/or coupled to the subject. In response to detecting the biometric condition, controlled release of the corresponding nanoparticulate matter is initiated, and the method ends. The release of the nanoparticulate matter in response to detecting the biometric condition is controlled according to at least one embodiment of the controlled release nanoparticulate matter delivery system described in detail above.

While the disclosure has been described with reference to a preferred embodiment or embodiments, it will be understood by those skilled in the art that various changes may be made and equivalents may be substituted for elements thereof without departing from the scope of the disclosure. In addition, many modifications may be made to adapt a particular situation or material to the teachings of the disclosure without departing from the essential scope thereof. Therefore, it is intended that the disclosure not be limited to the particular embodiment disclosed as the best mode contemplated for carrying out this disclosure, but that the disclosure will include all embodiments falling within the scope of the appended claims.

What is claimed is:

1. A method of releasing nanoparticulate matter contained in a thermoresponsive polymer, the method comprising:

determining a desired release rate at which to release the nanoparticulate matter;

determining a desired temperature at which the nanoparticulate matter is released at the desired release rate;

determining an actual temperature of the thermoresponsive polymer;

comparing the actual temperature to the desired temperature; and adjusting the actual temperature of the thermoresponsive polymer to release of the nanoparticulate matter at the desired release rate selectively applying a plurality of heating cycles and cooling cycles to a hydrocomposite carrier so to deliver the nanoparticulate, matter from the hydrocomposite carrier at the desired release rate, wherein adjusting the actual temperature comprises supplying electrical current to a thermoelectric device having a variable temperature surface that controls the actual temperature of the thermoresponsive polymer, and controlling the current to flow the current in a first direction during the heating cycles and a second direction having an opposite direction than the first direction during the cooling cycles to adjust the actual temperature and maintain the desired release rate;

controlling the current supplied to the thermoelectric device based on al least on of the comparison and at least on biometric condition to control the release of the nanoparticulate matter.

2. The method of claim 1, further comprising controlling release of a first nanoparticulate matter contained in a first thermoresponsive polymer independently from release of a second nanoparticulate matter contained in a second thermoresponsive polymer different from the first thermoresponsive polymer.

3. The method of claim 1, further comprising adjusting the actual temperature of at least one thermoresponsive polymer based on the at least one biometric condition.

4. The method of claim 3, wherein the biometric condition includes at least one of body temperature, body perspiration, body vibration, breathing, heart rate and sound.

5. The method of claim 1, wherein supplying the electrical current comprises:

generating a first voltage having a first polarity that induces the current to flow in the first direction through the thermoelectric device to heat the thermoresponsive polymer; and generating a second voltage having a second polarity that induces the current to flow in the second direction opposite the first direction through the thermoelectric device to cool the thermoresponsive polymer.

6. The method of claim 5, further comprising:

operating the thermoelectric device in a heating mode to actively heat the variable temperature surface when the current flows in the first direction; and operating the thermoelectric device in a cooling mode to cool the variable temperature surface when the current flows in the second direction.

* * * * *